United States Patent [19]
Norton et al.

[11] Patent Number: 5,681,873
[45] Date of Patent: Oct. 28, 1997

[54] BIODEGRADABLE POLYMERIC COMPOSITION

[75] Inventors: Richard L. Norton; Stephen Michael Gregory Knight, both of Fort Collins, Colo.; Arthur J. Tipton, Birmingham, Ala.

[73] Assignee: Atrix Laboratories, Inc., Fort Collins, Colo.

[21] Appl. No.: 136,659

[22] Filed: Oct. 14, 1993

[51] Int. Cl.$^6$ .................... A61F 2/28; A61F 2/02
[52] U.S. Cl. .............. 523/115; 523/105; 523/113; 523/114; 424/426; 424/486; 528/354
[58] Field of Search .................. 523/105, 124, 523/113–115; 524/284, 381, 394, 425, 423, 414, 47, 48, 415; 424/426, 428

[56] References Cited

U.S. PATENT DOCUMENTS

| | | | |
|---|---|---|---|
| Re. 32,208 | 7/1986 | Mattei et al. | 424/78 |
| 2,155,658 | 4/1939 | Herrmann | 514/772.2 |
| 3,068,188 | 12/1962 | Beste | 524/173 |
| 3,219,527 | 11/1965 | Gurney | 424/435 |
| 3,328,246 | 6/1967 | Gottfried | 424/435 |
| 3,458,622 | 7/1969 | Hill | 424/19 |
| 3,767,784 | 10/1973 | Glick | 128/156 |
| 3,887,699 | 6/1975 | Yolles | 424/477 |
| 3,931,678 | 1/1976 | O'Sullivan | 433/228.1 |
| 3,975,350 | 8/1976 | Hudgin et al. | 260/30.4 N |
| 4,088,798 | 5/1978 | Michaelis | 427/3 |
| 4,127,127 | 11/1978 | Wong | 128/260 |
| 4,161,948 | 7/1979 | Bichon | 128/156 |
| 4,294,753 | 10/1981 | Urist | 260/112 R |
| 4,379,914 | 4/1983 | Lundberg | 528/354 |
| 4,439,420 | 3/1984 | Mattei et al. | 424/78 |
| 4,440,789 | 4/1984 | Mattei et al. | 424/78 |
| 4,443,430 | 4/1984 | Mattei et al. | 424/78 |
| 4,447,562 | 5/1984 | Ivani | 523/105 |
| 4,450,150 | 5/1984 | Sidman | 424/426 |
| 4,451,452 | 5/1984 | Deibig et al. | 424/78 |
| 4,455,256 | 6/1984 | Urist | 260/112 R |
| 4,491,479 | 1/1985 | Launchenauer | 128/156 |
| 4,526,909 | 7/1985 | Urist | 523/115 |
| 4,563,489 | 1/1986 | Urist | 524/21 |
| 4,568,536 | 2/1986 | Kronenthal | 514/900 |
| 4,570,629 | 2/1986 | Widra | 128/156 |
| 4,582,640 | 4/1986 | Smestad | 128/DIG. 8 |
| 4,595,713 | 6/1986 | St. John | 523/105 |
| 4,596,574 | 6/1986 | Urist | 623/16 |
| 4,614,787 | 9/1986 | Szycher | 528/75 |
| 4,619,989 | 10/1986 | Urist | 530/417 |
| 4,631,188 | 12/1986 | Stoy | 424/81 |
| 4,650,665 | 3/1987 | Kronenthal | 424/435 |
| 4,677,139 | 6/1987 | Feinmann | 128/90 |
| 4,715,369 | 12/1987 | Suzuki | 424/435 |
| 4,745,160 | 5/1988 | Churchill | 523/105 |
| 4,761,471 | 8/1988 | Urist | 530/350 |
| 4,767,627 | 8/1988 | Caldwell | 424/426 |
| 4,772,470 | 9/1988 | Inoue | 424/435 |
| 4,774,227 | 9/1988 | Piez | 128/DIG. 8 |
| 4,789,732 | 12/1988 | Urist | 530/350 |
| 4,795,804 | 1/1989 | Urist | 530/350 |
| 4,857,456 | 8/1989 | Urist | 530/350 |
| 4,894,373 | 1/1990 | Young | 435/7 |
| 4,902,296 | 2/1990 | Bolander et al. | 514/239.2 |

(List continued on next page.)

FOREIGN PATENT DOCUMENTS

| | | | |
|---|---|---|---|
| 1 260 488 | 9/1989 | Canada. | |
| 0 140 766 | 5/1985 | European Pat. Off. | 424/435 |
| 0 537 559 A1 | 4/1993 | European Pat. Off.. | |
| 0 539 751 A1 | 5/1993 | European Pat. Off.. | |
| 0 560 014 A1 | 9/1993 | European Pat. Off.. | |
| 0 649 662 A1 | 4/1995 | European Pat. Off.. | |
| 29 17 037 | 4/1980 | Germany | 433/228.1 |
| 3 825 211 | 2/1990 | Germany. | |
| NZ 226514 | 2/1990 | New Zealand. | |
| 2223027 | 8/1989 | United Kingdom. | |

OTHER PUBLICATIONS

"Poly(caprolactone)diol", M.W. 1250 and 2000, Aldrich Chemical Catalog, p. 1241, 1988–1989.

Encyclopedia of Polymer Science and Engineering, vol. 2, pp. 236–237 (Biodegradable Polymers), John Wiley & Sons, Inc. (1985).

Billmeyer, Textbok of Polymer Science (Third Edition), pp. 390–391, John Wiley & Son, New York.

Gilding, Biodegradable Polymers (Chapter 9), pp. 210–232, Biocompatibilty of Clinical Implant Materials.

Hawley's Condensed Chemical Dictionary (11th Ed.) pp. 224, 555 and 567, Van Nostrand Reinhold Co., NY, NY.

Holland, Polymers for Biodegradable Medical Devices, 1. The Potential of Polyesters and Controlled Macromolecular Release Systems, J. of Controlled Release 4: 155–180 (1986).

K. Juni et al., *Chem. Pharm Bull.*, 33:1609 (1985).

Baldauf, et al., "The Use of Bone Wax", *J. Foot Surgery*, 25, 456–458 (1986).

Bertrand et al., *Actualities Odonto–Stomatologiques*, (39), 713–730 (1985).

Howard, et al., "The Effect of Bone Wax on the Healing of Experimental Rat Tibial Lesions", *Clinical Orthopaedics and Related Research*, 63, 226–232 (1969).

Solheim, Eirik et al., "Effect of Local Hemostatics on Bone Induction in Rats: A Comparative Study of Bone Wax, Fibrin–Collagen Paste, and Bioerodible Polyorthoester With and Without Gentamicin", *J. Biomed. Mat. Res.*, 26, 791–800 (1992).

(List continued on next page.)

*Primary Examiner*—Tae Yoon
*Attorney, Agent, or Firm*—Merchant & Gould, Smith, Edell, Welter & Schmidt

[57] ABSTRACT

The invention provides moldable, biodegradable composition for use with bone and other tissues. The composition comprises a poly(caprolactone) thermoplastic polymer processed alone or compounded with a biocompatible, biodegradable substance that controls crystallization of the polymer and functions to soften the composition. The composition may further include a biologically-active agent such as an antibiotic for sustained delivery in an animal, a coloring agent for tinting the composition, and other additives as desired.

17 Claims, No Drawings

U.S. PATENT DOCUMENTS

| | | | |
|---|---|---|---|
| 4,904,478 | 2/1990 | Walsdorf et al. | 623/16 |
| 4,905,680 | 3/1990 | Tunc | 424/468 |
| 4,911,931 | 3/1990 | Baylink | 606/69 |
| 4,916,241 | 4/1990 | Hayward et al. | 424/606 |
| 4,920,203 | 4/1990 | Tang | 523/105 |
| 4,921,697 | 5/1990 | Peterlik et al. | 549/313 |
| 4,932,973 | 6/1990 | Gendler | 424/85.5 |
| 4,933,182 | 6/1990 | Higashi | 424/435 |
| 4,938,763 | 7/1990 | Dunn et al. | 604/891.1 |
| 4,939,131 | 7/1990 | Benedict et al. | 623/16 |
| 4,942,157 | 7/1990 | Gall et al. | 514/102 |
| 4,946,870 | 8/1990 | Partain, III et al. | 514/108 |
| 4,961,707 | 10/1990 | Magnusson et al. | 514/777 |
| 5,077,049 | 12/1991 | Dunn et al. | 424/426 |
| 5,143,730 | 9/1992 | Fues et al. | 424/426 |
| 5,238,978 | 8/1993 | Stein | 523/351 |
| 5,278,201 | 1/1994 | Dunn et al. | 523/113 |
| 5,278,202 | 1/1994 | Dunn et al. | 523/113 |
| 5,308,623 | 5/1994 | Fues et al. | 424/426 |
| 5,324,519 | 6/1994 | Dunn et al. | 424/426 |
| 5,324,520 | 6/1994 | Dunn et al. | 424/435 |
| 5,340,849 | 8/1994 | Dunn et al. | 523/113 |
| 5,368,859 | 11/1994 | Dunn et al. | 424/426 |
| B1 4,938,763 | 7/1995 | Dunn et al. | 604/891.1 |

OTHER PUBLICATIONS

Sorrenti et al., "Reaction of the Human Tibia to Bone Wax", *Clinical Orthopaedics and Related Research*, 182, 293–296 (1984).

Sudmann et al., "use of New Hemostatis, Biodegradable Polymer Versus Bone Wax Made of Beeswax—A Clinical and Experimental Study", *Acta Orthop Scand*, 61, 63–64 (1990).

BIODEGRADABLE POLYMERIC COMPOSITION

STATEMENT REGARDING FEDERALLY-FUNDED AND SPONSORED RESEARCH

This invention was made with government support from the Department of the Army, U.S. Army Institute of Dental Research, under Contract No. DAMD17-90-C-0017. The government may have certain rights in this invention.

BACKGROUND OF THE INVENTION

Various compositions have been formulated for use by doctors and other health care professionals to control bleeding from cut bone. One such material is bone wax, typically made of a combination of refined beeswax and a softening agent such as a hydrocarbon or vegetable oil. In use, bone wax is softened by applying heat or by manually manipulating the material, and then applied to a bone surface over the site of bleeding. Hemostasis is achieved by a tamponade action by plugging of osseous vessels and sinuses.

A drawback of conventional bone wax is its brittle character at room temperature and the need to heat it for proper handling. Also, bone wax does not adhere well to bone surfaces thus providing inadequate hemostasis. In addition, the beeswax component cannot be absorbed by the body and will persist within the implant site long after its usefulness has passed, interfering with bone regrowth or acting as a source of infection or inflammation in the defect site. Also, conventional bone waxes are typically white in color, making it difficult to see in situ on a bone surface.

Attempts have been made to overcome the problem of non-absorbability of bone wax in the body by substituting a biodegradable or bioabsorbable material for the beeswax component. For example, U.S. Pat. No. 5,143,730 to Fues et al., describes a resorbable, viscous to solid wax made of oligomers of glycolic acid and/or lactic acids combined with monohydroxyl and/or polyhydroxyl alcohols and/or a corresponding carboxylic acid, and further with an organic or inorganic salt such as calcium palmitate, hydroxy apatite, calcium carbonate or calcium glycolate. U.S. Pat. No. RE 32208 to Mettei et al., describes an absorbable composition having a putty-like consistency at room temperature, made of a biocompatible fatty acid salt, i.e., calcium stearate, in a body absorbable base such as an ethylene oxide/propylene oxide block copolymer, a polyethylene glycol, methoxypolyethylene glycol, triglyceride, or fatty acid ester. A drawback of these materials is that their consistency is either too hard or too fluid, making it difficult to manipulate and apply the material to a defect site. In addition, these materials do not adhere properly to a bone surface, and do not provide an effective level of hemostasis in the defect site.

Therefore, an object of the invention is to provide a composition which may be applied to bone or other tissue, and is biodegradable and/or is bioabsorbable inside the body and is capable of providing an effective level of hemostasis of a tissue laceration. Another object is to provide a biodegradable, thermoplastic composition that can be readily manipulated and shaped by hand to form a device for covering a bone or other tissue defect, which can be formulated to remain intact in the defect for long periods or break into small pieces rapidly after hemostasis has been achieved. Another object is to provide a biodegradable thermoplastic composition that is moldable or spreadable for other medical device applications such as a temporary barrier between tissues or a temporary space filler. Another object is to provide a device to perform the above objects and simultaneously deliver a bioactive material locally or systemically in the body. Yet another object is to provide an implant for delivering a bioactive material locally or systemically in the body.

SUMMARY OF THE INVENTION

These and other objects are achieved by the present invention which is directed to a moldable, biodegradable thermoplastic composition suitable for use with bone or other tissue, and a method for using the composition.

The composition is composed of a poly(caprolactone) thermoplastic polymer that has been polymerized or processed so as to alter the crystalline structure of the polymer. The poly(caprolactone) polymer may be combined with a biocompatible, biodegradable agent that controls crystallization of the polymer and functions to soften the composition. According to the invention, the processing of the poly(caprolactone) polymer, optionally with a crystallization-controlling agent, effects homogeneity of the polymer mass to produce a composition in which the crystalline regions of the polymer are substantially uniformly distributed throughout. The composition is formulated to provide a moldable mass that can be applied to the surface of a bone or other tissue, preferably by smearing onto the tissue surface, and will adhere and remain attached to the bone or other tissue surface to provide an effective amount of hemostasis, and/or facilitate effective healing of the tissue defect. The composition has a level of stability and cohesiveness such that it will remain essentially intact in the defect during the initial phase of wound repair to prevent bleeding, and eventually degrade as the healing of the defect progresses.

The poly(caprolactone) polymer ingredient of the composition is a solid with a weight average molecular weight of about 600–3000, preferably about 800–2500. The poly(caprolactone) polymer itself is a waxy solid with poor cohesion, in which part of its mass is a paste-like consistency and part is a hard, dense consistency. According to the invention, when the poly(caprolactone) is melted and cooled under controlled conditions of temperature and time, with or without a crystallization-controlling agent, a moldable, waxen mass with a uniform, and preferably spreadable, consistency is produced wherein the crystalline regions of the polymer are uniformly distributed throughout.

A crystallization-controlling agent may optionally be combined with the poly(caprolactone) polymer to effect homogeneity of the polymer mass, that is, a substantially uniform distribution of crystalline sections of the polymer to achieve a homogeneous mass having the desired physical characteristics of moldability, cohesion, and stability for effective use with bone and other tissues. The crystallization-controlling agent may be in the form of a dispersed solid particle in the composition, for example, an inorganic salt such as calcium carbonate or calcium phosphate, a polymer such as poly(vinyl alcohol), starch or dextran, and other like substance. Other useful crystallization-controlling agent are those substances that are either melted with the poly(caprolactone) during the compounding process, or soluble in the molten poly(caprolactone) polymer. Examples of those substances include low molecular weight organic compounds such as glycerol palmitate or ethyl lactate, polymers such as poly(ethylene glycol) or poly(lactide-co-caprolactone), and other like substances. Compositions formulated with a crystallization-controlling agent include about 40–95 wt-% of the poly(caprolactone) polymer, preferably about 60–90 wt-%, and about 5–60 wt-% of the crystallization-controlling agent, preferably about 10–40 wt-%.

The composition may also include a biologically-active agent, as for example, an antibacterial or antifungal agent for providing a therapeutic effect by treating and preventing infections in the implant site or systemically in the body, a growth factor or hormone for providing a physiological effect in the body, and other like agents. With the inclusion of a biologically-active agent, the composition may serve as a system for sustained, controlled delivery of the agent in vivo to the animal.

The composition may also include other additives and adjuvants as desired. For example, a coloring agent may be included to tint and enhance visualization of the composition in the bone or other tissue defect. A release rate modification agent, such as dimethyl citrate, ethyl heptanoate or glycerin, may be included in the composition for controlling the rate of breakdown or degradation of the composition and/or the rate of release of a biologically agent in vivo from the composition. In addition, a pore forming agent such as a sugar, salt or polymer, may be included to generate pores in the matrix of the hardened composition in situ.

The composition is adherent to bone and provides for effective hemostasis to stop the flow of blood and prevent blood loss from a cut bone. The polymer material is retained within the defect for a time effective to allow regrowth of bone tissue, and provides a matrix for bone ingrowth if it is porous. The compositions are biocompatible and biodegradable in the body of the animal, gradually degrading over time. The composition may also be applied to a tissue to provide for sustained delivery and controlled release of a bioactive agent in vivo. For in vivo use, it is preferred that the composition is sterilized prior to applying it to the site, for example, by gamma irradiation, and the like.

DETAILED DESCRIPTION OF INVENTION

As used herein, the term "biodegradable" means that the composition will degrade over time by the action of enzymes, by hydrolyric action and/or by other similar mechanisms in the human body. By "bioerodible," it is meant that the composition will erode or degrade over time due, at least in part, to contact with substances found in the surrounding tissue fluids, cellular action, and the like. By "bioabsorbable," it is meant that the composition will be broken down and absorbed within the human body, for example, by a cell, a tissue, and the like.

The present invention provides a biodegradable and bioerodible composition for use in repairing and healing defects in bone and other tissues in an animal. The composition has a moldable, waxen-like character, and a consistency that allows it to be easily molded and/or spread onto the surface of a tissue defect such as a bone defect. The composition will adhere to the surface of the bone or other tissue defect, when wet or dry, and provide an amount of hemostasis to effectively stop bleeding in or from the defect.

The composition will persist as a cohesive mass in the defect site for a time effective to facilitate hemostasis. After facilitating hemostasis, the composition will either fragment into small pieces or gradually degrade by the action of tissue fluids, and other like mechanisms, depending upon the formulation of ingredients. The material will not interfere with healing of the defect or tissue regeneration, and may facilitate healing and tissue regeneration by action of the crystallization-controlling agent and/or one or more additives included in the composition. Aside from facilitating hemostasis and enhancing cell growth and tissue regeneration, the composition may also be used for delivering biologically-active agents such as drugs and medicaments, locally or systemically, in the body of the animal.

Poly(caprolactone) thermoplastic polymer. The major ingredient in the present compositions is a biodegradable, solid, poly(caprolactone) thermoplastic polymer that has a weight average molecular weight of about 600–3000, preferably about 800–2000, preferably about 1000–2000. Preferred poly(caprolactones) include PCL diol MW 1250 and PCL diol MW 2000, which are hard waxy solids and available commercially, for example, from Aldrich Chemical Company, Inc., Milwaukee, Wis. Also preferred is a poly(caprolactone) prepared with propylene glycol as the initiator and having an inherent viscosity of about 0.10 dl/g. Also useful are poly(caprolactones) prepared with other polyhydroxyl initiators such as glycerol and low molecular weight poly(ethylene glycol).

The composition may be formulated with the poly(caprolactone) polymer alone without a crystallization-controlling agent if the composition is processed using conditions such as cooling temperatures and times effective to control crystallization and produce a composition that has a homogenous and moldable consistency. The composition may also be formulated with the solid poly(caprolactone) polymer combined with one or more crystallization-controlling agents in an amount effective to control crystallization and soften the composition. The latter composition contains about 40–95 wt-% of the poly(caprolactone) polymer, preferably about 60–90 wt-%, preferably about 75–85 wt-%, and about 5–60 wt-% of one or more crystallization-controlling agents, preferably about 10–50 wt-%, preferably about 25–35 wt-%.

Crystallization-Controlling Agent. Crystallization-controlling agents suitable for use in the present compositions may be divided into two major classes, those that persist in the form of a solid particulate in the molten poly(caprolactone)-based composition, and those that melt or dissolve in the molten polymer composition.

Crystallization-controlling agents that will persist as solid particles, or fillers, in the composition include inorganic or organic salts, and polymers. Suitable inorganic salts include, for example, calcium carbonate, hydroxy apatite, calcium phosphate, calcium apatite, calcium sulfate, calcium bicarbonate, calcium chloride, sodium carbonate, sodium bicarbonate, sodium chloride, and other like salts. Suitable organic salts include for example, calcium stearate, calcium palmitate, sodium stearate, other metallic salts of $C_{12}$–$C_{12}$ fatty acid derivatives, and other like salts. Polymers suitable for use in the composition that persist as dispersed particles or fillers in the composition include, for example, polysaccharides, cellulose derivatives and poly(vinyl alcohol). Examples of suitable polysaccharides include, for example, dextran, maltodextrin, starches derived from corn, wheat, rice and the like, and starch derivatives such as sodium starch glycolate. Examples of suitable cellulose derivatives include for example, sodium carboxymethyl cellulose, crosslinked sodium carboxymethyl cellulose, carboxyl methyl cellulose, hydroxyethyl cellulose, and the like. Suitable poly(vinyl alcohol)s have a molecular weight of about 5,000 to 20,000, preferably about 10,000–15,000, with a percent hydrolysis of about 80–100%.

Crystallization-controlling agents which either melt with or dissolve into the molten poly(caprolactone) during compounding may also be used in the polymer compositions of the invention. These compositions may or may not undergo some degree of phase separation during cooling.

Crystallization-controlling agents of this type include low molecular weight organic compounds and polymers. Suitable low molecular weight compounds include, for example, glycerol, palmitate, glycerol stearate and other like glycerol derivatives, triethyl citrate and other like citric acid derivatives, ethyl lactate and other like esters, and the like. Examples of suitable polymers include, for example, poly (ethylene glycol) with a molecular weight of about 1,500–10,000, with about 2,000–4,000 being preferred; poly (vinyl pyrrolidone) with a molecular weight of about 5,000–20,000; poly(lactide-co-caprolactone) with a lactide content of about 1–75% and a caprolactone content of about 25–99%, and an inherent viscosity in chloroform of about 0.05–0.40 deciliter/gram; and other poly(caprolactones). Other polymers suitable for use in the present compositions include copolymers of the above-mentioned polymers or end-group modified versions of these polymers such as polyethylene glycol monostearate. One or more poly (caprolactones) having a molecular weight different from the major poly(caprolactone) thermoplastic component may also be used as a crystallization-controlling agent. For example, the composition may be formulated with two or more poly(caprolactones) of differing molecular weight to provide a broader molecular weight distribution in order to vary the physical properties of the blend and provide a composition that is moldable and smearable.

The crystallization-controlling agent is included in the composition in an amount effective to soften the solid poly(caprolactone) polymer to a moldable and/or smearable consistency, and to enhance the property of hemostasis of the composition in a bone or other tissue defect. Preferably, the crystallization-controlling agent is a non-solvent, solid substance. A crystallization-controlling agent may be included in the composition alone or in combination with another crystallization-controlling agent. An example of a preferred combination of such agents is poly(lactide-co-caprolactone) and calcium stearate.

Examples of preferred compositions according to the invention are those composed of about 70–80% PCL MW 1250 and about 20–30% polyvinyl alcohol (PVA); about 70–80% PCL MW 1250 and about 20–30 % PEG 3350; or about 80–90% PCL MW 1250 and about 10–20% calcium carbonate.

Preparation of the Compositions. The poly(caprolactone) and one or more crystallization-controlling agent, and/or other additives, as desired, are compounded by melting the poly(caprolactone) and combining the other ingredients of the formulation with the molten polymer. The crystallization-controlling agent, and/or other additives, may be added to the poly(caprolactone) before melting, or to the molten polymer. The poly(caprolactone) will become molten above approximately 50° C., the exact temperature varying with the molecular weight and/or the structure of the polymer, which information is known in the art. The mixing temperature may be varied from about 40°–70° C. A use of a lower mixing temperature will increase the viscosity of the mixture, which aids in keeping certain ingredients suspended in the mix.

The preparation of small batches of the composition may be achieved, for example, by combining the ingredients in a container such as a vial, placing the vial in a water bath, and mixing the ingredients with a spatula, stick or other device. Larger batches may be prepared, for example, using a double planetary mixer or other like equipment capable of heating and mixing a fluid mixture. Small batches may be cooled and stored in the vial or other container in which the composition was prepared, whereas larger batches are preferably divided into small, individual units, either before or after cooling. Small amounts of the composition may be stored or packaged in a vial made, for example of glass, plastic or other like material, or a pouch made of a plastic, metallic foil, or a combination thereof, and other like materials, or other suitable packaging. Depending on the packaging material, the composition may be placed into the package while molten or after solidification. The composition may be in the form of a sphere, chips, a thin sheet, and/or any other form as desired.

The molten mixture is cooled or annealed under controlled conditions to achieve the desired physical properties for the composition, namely, moldable, smearable, cohesive, and uniform. To prepare a composition containing the poly (caprolactone) alone, or the polymer in combination with a crystallization-controlling agent and/or other additive, cooling or annealing conditions are controlled, particularly the temperature and time. The size (i.e., volume, thickness, shape) and proximity of the samples to each other during the cooling and annealing process are also controlled to achieve substantially uniform cooling or annealing of a composition throughout its mass. The cooling or annealing temperature is about 30°–50° C., preferably about 35°–45° C., and the cooling or annealing time is about 1–72 hours, preferably about 12–24 hours. The composition is then allowed to cool to room temperature. Properly mixed and cooled or annealed compositions are characterized as being cohesive with a uniform, or homogenous consistency throughout its mass. Improperly cooled or annealed formulations are less cohesive and contain soft and hard regions in the composition. Although not intended to be a limitation of the present invention, it is believed that the effect of the annealing in combination with a crystallization-controlling agent in the composition, effectively controls crystallization of the poly (caprolactone). Homogeneity of the physical properties of the composition requires a substantially uniform distribution of crystalline regions of poly(caprolactone) throughout the composition. The overall amount of crystallinity, the number and size of the crystalline regions plus the degree of order in the crystalline regions will also affect the physical properties of the composition. The crystallization-controlling agent can also affect the physical properties of the composition, for example, graininess, smoothness, stickiness, and the like.

The composition may be made more easily moldable or spreadable by kneading the composition, for example, with the fingers, just before use. This kneading can also improve the uniformity of the consistency of the composition. The kneading may be achieved, for example, by alternately squeezing and rolling a small portion of the composition using two or three fingers and the thumb of a gloved hand. This composition may be worked in this way for a few seconds to one or two minutes until the desired consistency is achieved. Such hand mixing of the composition achieves a uniform consistency due to both the mechanical action of the kneading process and the heating effect by the contact with a warm object, i.e., hands.

Dyes. A coloring agent may be included to tint the composition so that it can be more easily observed in the defect site. Examples of suitable coloring agents include dyes such as Acid Orange 7 (D&C Orange No. 4), Basic Violet 10 (Rhodamine B; D&C Red No. 19), Acid Yellow 23 (D&C Yellow No. 5), Acid Yellow 17, Solvent Green 3 (D&C Green No. 6), Solvent Violet 13 (D&C Violet No. 2), Metanil Yellow (Acid Yellow 36), Acid Blue 9 (D&C Blue No. 1), Acid Green 25 (D&C Green No. 5), and the like, commercially available from Aldrich Chemical Company, Inc., Milwaukee, Wis. The composition may include about 0.01–1. wt-% of a coloring agent, preferably about 0.05–0.1 wt-%. The dye may be added to the composition at any step in the compounding process.

Biologically-active Agent. Optionally, the composition may include a biologically-active agent, or bioactive agent, either singly or in combination, to provide delivery of the agent to adjacent or distant tissues and organs in the animal. Biologically-active agents which may be used alone or in combination in the composition include, for example, a medicament, drug, or other suitable biologically-, physiologically-, or pharmaceutically-active substance which is capable of providing local or systemic, biological, physiological or therapeutic effect in the body of an animal including a mammal, and of being released from the composition into adjacent or surrounding tissue fluids. The biologically-active agent may stimulate a biological or physiological activity within the animal. For example, the agent may act as an antibiotic, enhance cell growth and tissue regeneration, function in birth control, cause nerve stimulation or bone growth, and the like.

The bioactive agent may be added to the composition during the compounding process while the poly (caprolactone), and optional crystallization-controlling agents are in a molten state, while the composition is cooling, or after the composition has cooled. If the bioactive agent is added after the composition has cooled, it may be incorporated into the composition by kneading the biologically-active agent and cooled composition together, for example, manually by hand or using a mortar and pestle, or other like device. Once the composition is placed into the bone defect or other site in the body, the biologically-active agent is released into the adjacent tissue fluids, preferably at a controlled rate. This release may result from diffusion of the biologically-active agent through and out of the composition, degradation of the composition, erosion of the composition, or a combination of these mechanisms. The release of the biologically-active agent from the matrix of the composition may be varied, for example, by the solubility of the biologically-active agent in aqueous tissue fluids, the distribution of the bioactive agent within the matrix, the size, shape, porosity, solubility and biodegradability of the composition, the type and amount of crystallization-controlling agent and/or an additive, and the like.

The polymer composition includes the biologically-active agent in an amount effective to provide the desired level of biological, physiological, pharmacological and/or therapeutic effect in the animal. There is generally no critical upper limit on the amount of the bioactive agent included in the composition. The only limitation is a physical limitation for advantageous application, i.e., the bioactive agent should not be present in such a high concentration that the consistency and handling or hemostatic property of the composition is adversely affected. The lower limit of the amount of bioactive agent incorporated into the composition will depend on the activity of the bioactive material and the period of time desired for treatment.

Suitable biologically-active agents for use in the invention includes substances useful in preventing an infection systemically in the animal or locally at the defect site, as for example, anti-inflammatory agents such as hydrocortisone, prednisone, and the like; anti-bacterial agents such as doxycycline, gentamicin, penicillin, cephalosporins, bacitracin, vancomycin, methicillin, cefazolin, and the like; antiparasitic agents such as quinacrine, chloroquine, and the like; antifungal agents such as nystatin, gentamicin, and the like; antiviral agents such as acyclovir, ribarivin, interferons, and the like. Also useful is a substance, or metabolic precursor thereof which is capable of promoting growth and survival of cells and tissues or augmenting the functioning of cells, as for example, a nerve growth promoting substance such as a ganglioside, a nerve growth factor, and the like; a hard or soft tissue growth promoting agent such as an osteoinductive growth factor, platelet-derived growth factor, insulin-like growth factor, transforming growth factor β, fibroblast growth factor, human growth factor, fibronectin (FN), human growth hormone (HGH), a colony stimulating factor, and the like; protein growth factor interleukin-1 (IL-1), and the like; and a bone growth promoting substance such as hydroxy apatite, tricalcium phosphate, and the like; antineoplastic agents such as methotrexate, 5-fluorouracil, tumor-specific antibodies conjugated to toxins, tumor necrosis factor, and the like; analgesic agents such as salicylic acid, acetaminophen, ibuprofen, flurbiprofen, morphine and the like; local anesthetics such as cocaine, benzocaine, bupivacaine, and the like; vaccines such as hepatitis, influenza, measles, rubella, tetanus, polio, rabies and the like; central nervous system agents such as a tranquilizer, B-adrenergic blocking agent, dopamine, and the like; hormones such as progesterone, follicle stimulating hormone, insulin, somatotropins, and the like; antihistamines such as diphenhydramine, chlorphencramine, and the like; cardiovascular agents such as digitalis, nitroglycerine papaverine, streptokinase and the like; anti-ulcer agents such as cimetidine hydrochloride, isopropamide iodide, and the like; bronchodilators such as metaproternal sulfate, aminophylline, and the like; vasodilators such as theophylline, niacin, minoxidil, and the like; and other like bioactive substances. For other examples of biologically-active agents that may be used in the present invention, see Applicants' corresponding U.S. patent application Ser. No. 07/783,512, filed Oct. 28, 1991, the disclosure of which is incorporated by reference herein.

Accordingly, the formed implant may function as a delivery system of drugs, medicaments and other biologically-active agents to tissues adjacent to or distant from the implant site, or as a combination of a medical device and delivery system. The biologically-active agent is preferably incorporated into the matrix of the composition, and subsequently released into surrounding tissue fluids and to the pertinent body tissue or organ.

Control of release of the bioactive agent. The rate of release of a biologically-active agent from the composition may be controlled by the inclusion of one or more additives that function as a release rate modification agent, and by varying the concentration of that substance. According to the invention, the inclusion of a particular crystallization-controlling agent in the composition may function similarly to a release rate modification agent, to alter the release of a bioactive agent from the composition.

For example, the inclusion of a release rate modification agent may cause the composition to fragment or degrade quickly, resulting in a rapid release of the bioactive agent from the implanted material, or may delay these processes and consequently slow release. Another mechanism of action is that diffusion of the bioactive agent through the matrix may be altered where the bioactive agent is more soluble in the release rate modification agent controlling agent than in the poly(caprolactone), or the release rate modification agent modifies the crystallinity or the nature of the amorphous regions of the poly(caprolactone), making the polymer more open to diffusion of the bioactive agent or to the influx of water to dissolve the bioactive agent. The release rate modification agent may also cause pores to form in the matrix which will increase the rate of release of a bioactive agent. The nature and amount of a release rate modification agent included in a composition are such that the physical properties of the composition in its particular application are not adversely affected or compromised.

The release rate modification agent may be, for example, an organic substance which is water-soluble, water-miscible, or water insoluble (i.e., water immiscible). The release rate modification agent is preferably an organic compound which will substitute as the complementary molecule for secondary valence bonding between polymer molecules, and increases the flexibility and ability of the polymer molecules to slide past each other. Such an organic compound preferably includes a hydrophobic and a hydrophilic region so as to effect secondary valence bonding. It is preferred that a release rate modification agent is compatible with the poly(caprolactone) polymer, or the polymer in combination with a crystallization-controlling agent, used to formulate the composition. It is further preferred that the release rate modification agent is a pharmaceutically-acceptable substance.

Useful release rate modification agents include, for example, fatty acids, triglycerides, other like hydrophobic compounds, organic solvents, and plasticizing compounds. Suitable release rate modification agents include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl) sebecate, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as $C_6$-$C_{12}$ alkanols, 2-ethoxyethanol, and the like. The release rate modification agent may be used singly or in combination with other such agents. Suitable combinations of release rate modification agents include, for example, glycerin/propylene glycol, sorbitol/glycerine, ethylene oxide/propylene oxide, butylene glycol/adipic acid, and the like. Preferred release rate modification agents include dimethyl citrate, triethyl citrate, ethyl heptanoate, glycerin, and hexanediol.

The amount of the release rate modification agent included in the composition will vary according to the desired rate of release of the bioactive agent from the composition in vivo. Preferably, the composition contains about 0.5–15%, preferably about 5–10%, of a release rate modification agent.

For other examples and further discussion of release rate modification agents, or rate modifying agents, for use in the present invention, see Applicants' corresponding U.S. patent application Ser. No. 07/776,816, filed Oct. 15, 1991, the disclosure of which is incorporated by reference herein.

Pore Forming Agent. When placed into the bone or other tissue defect in an animal, the composition is a solid structure. Optionally, the composition may include a pore-forming agent to generate pores in the polymer matrix to achieve a microporous structure. The pore-forming agent may be any pharmaceutically-acceptable, organic or inorganic, water-soluble substance that is substantially miscible in water and body fluids, and will dissipate from the solid matrix of the composition in situ into surrounding body fluids at the defect site. Suitable pore forming agents that may be used in the polymer composition include, for example, sugars such as sucrose and dextrose, salts such as sodium chloride and sodium carbonate, polymers such as hydroxylpropylcellulose, carboxymethylcellulose, polyethylene glycol, and polyvinylpyrrolidone, and the like. Solid crystals that will provide a defined pore size, such as salt or sugar, are preferred.

When the composition is applied to a tissue defect site, the pore forming agent may dissipate into surrounding tissue fluids over a short time following placement, or over an extended time period by the biodegradation or bioerosion of the composition in situ. Preferably, the pore-forming agent dissipates from the composition over an extended time in order to achieve the proper amount of hemostasis in the tissue defect.

Porosity of the matrix of the composition may be varied by the concentration of a water-soluble or water-miscible pore-forming agent in the polymer composition. For example, a high concentration of water-soluble substances in the thermoplastic composition may produce a polymer matrix having a high degree of porosity. The concentration of the pore forming agent relative to polymer in the composition may be varied to achieve different degrees of pore-formation, or porosity, in the matrix. Generally, the polymer composition will include about 0.01–1 gram of a pore forming agent per gram polymer.

The size or diameter of the pores formed in the matrix of the composition may be modified according to the size and/or distribution of the pore-forming agent within the polymer matrix. For example, pore-forming agents that are relatively insoluble in the polymer mixture may be selectively included in the polymer composition according to particle size in order to generate pores having a diameter that corresponds to the size of the pore forming agent. Pore forming agents that are soluble in the polymer mixture may be used to vary the pore size and porosity of the implant matrix by the pattern of distribution and/or aggregation of the pore forming agent within the polymer mixture and solid polymer matrix.

Where the composition is used to promote guided tissue regeneration, it is preferred that the diameter of the pores in the matrix of the composition are effective to deter growth of epithelial cells and enhance growth of connective tissue cells into the matrix of the composition. It is further preferred that the size of the pores and porosity of the matrix of the composition facilitate diffusion of nutrients and other growth-promoting substances such as growth factors, to cells which have grown into the matrix. The degree of porosity of the composition provides a matrix that will possess an effective amount of structural integrity for the desired period of time without breakage or fracturing in the defect site during restoration of the site.

To provide an effective device for bone cell regrowth and tissue regeneration, it is preferred that the diameter of the pores in the matrix of the composition in situ is about 3–500 microns, more preferably about 3–200 microns, more preferably about 75–150 microns. It is further preferred that the matrix of the composition has a porosity of about 5–95%, preferably about 25–85%, in order to provide optimum cell and tissue ingrowth into the matrix and optimum structural integrity.

Pore diameter and distribution within the matrix of the composition may be measured, as for example, according to scanning electron microscopy methods by examination of cross-sections of the polymer matrix. Porosity of the matrix may be measured according to suitable methods known in the art, as for example, mercury intrusion porosimetry, specific gravity or density comparisons, calculation from scanning electronic microscopy photographs, and the like.

Additionally, porosity may be calculated according to the proportion or percent of water-soluble material included in the polymer composition.

Use of the Composition. The poly(caprolactone)-based polymer compositions of the present invention are used for treating a tissue defect in an animal. For example, the composition may be used in a method for treating a bone tissue defect such as an arm or leg bone fracture, a sternotomy, a bone graft, a bone graft donor site, a tooth defect, and the like. The composition may be molded by hand to fit the defect site, and then placed onto the surface of the bone, preferably having a dry surface to provide hemostasis to stop bleeding from the bone, and to promote healing and regrowth of tissue in the defect.

Where used in an animal, the composition is preferably sterilized prior to its application to the bone or other tissue defect, for example by gamma radiation or other ionizing radiation, by gas sterilization using, for example, ethylene oxide, and the like. Preferably, the composition is sterilized using gamma radiation. The composition may then be packaged in sterilized container such as a plastic packaging, and stored at about 0°-30° C. until use.

The composition containing the poly(caprolactone) polymer and optionally, one or more crystallization-controlling agents, release rate modification agent, pore-forming agent, and other additives, may be varied according to the desired duration or time interval for maintaining the composition within the defect site, as for example, a few days or weeks to several years. When the composition is used to enhance cell growth and tissue regeneration, it is preferred that the composition will disintegrate at a rate effective to allow displacement of the matrix by cell growth from the adjacent cells or tissue.

For example, a composition containing a high molecular weight poly(caprolactone), such as MW 2500, may require a longer period of time for biodegradation in the defect site than a composition containing a low initial weight average molecular weight poly(caprolactone) such as MW 1250. Furthermore, variations in the poly(caprolactone) end groups may also affect the degradation rate of the composition in situ. For example, a poly(caprolactone) having a carboxylic end group will degrade at a faster rate than a poly(caprolactone) having a hydroxy end group.

The nature of the ingredients combined with the poly (caprolactone) may also affect degradation of the composition. For example, poly(vinyl alcohol) may cause fragmentation of the composition in situ which breaks the matrix apart and exposes additional surface area to body fluids which may hasten biodegradation. Hydrophilic substances tend to increase intake of water by the composition and subsequent hydrolysis. Hydrophobic substances tend to have the reverse effect. A substance that is an acid or base may catalyze the hydrolysis of the polymer.

Formulation of the composition and in vivo administration will ultimately be according to the judgment and protocol of the patient's attending health care professional such as a physician, or if appropriate, a dentist. Choice of the particular formulation of ingredients will be made by the attending health care professional. Without a bioactive agent, the composition can function as a structure for hemostasis and/or for promotion of cell growth and tissue repair. With a bioactive agent, the composition will not only function in such capacity but will also adopt the properties of the bioactive agent. The composition, with or without a bioactive agent, may also be used in combination with other medical devices such as screws, rods, plates, sutures, staples, surgical clips, meshes and fabrics, and the like, to enhance the properties of the device.

The amounts and concentrations of ingredients in the composition administered to the patient will generally be effective to accomplish the task intended. If that task is to fill a void space of a bone or other tissue defect, the composition will be prepared with an appropriate size and an effective amount of ingredients to accomplish this task. For administration of a bioactive agent, the amounts and release rates will follow recommendations of the manufacturer of the bioactive agent. Generally, the concentration of a bioactive agent in the composition will be about 0.01–400 mg per gram.

The invention will be further described by reference to the following detailed examples, wherein the methodologies are as described below. These examples are not meant to limit the scope of the invention that has been set forth in the foregoing description. Variation within the concepts of the invention are apparent to those skilled in the art. The disclosures of the cited references are incorporated by reference herein.

EXAMPLE 1

Preparation and Testing of Poly(caprolactone)-based Compositions

Poly(caprolactone) (PCL diol MW 1250), which had a pasty consistency, and PCL diol MW 2000, a hard waxy solid, were each combined with various substances (i.e., crystallization-controlling agents) to achieve a smooth consistency.

The PCL-based compositions were prepared by weighing the PCL polymer and the crystallization-controlling agent into a glass vial. The vials were placed into a heated water bath (65° C.) to melt the PCL polymer, and the ingredients stirred together with a wooden rod. The mixtures were placed in a 37° C. environmental shaker to cool slowly overnight.

The PCL-based formulations are shown in Table 1, below.

TABLE 1

| No. | I.D. | PCL Polymer[1] | Crystallization-Controlling Agent[2] |
|-----|------|----------------|--------------------------------------|
| 1 | 48-D | 76% PCL 1250 | 24% Glycerol Monopalmitate |
| 2 | 6-22-AG | 77% PCL 1250 | 23% Polyvinyl Alcohol |
| 3 | 6-22-AE | 77% PCL 1250 | 21% PEG 2000 |
| 4 | 54-C | 82% PCL 1250 | 18% PEG 400 Monostearate |
| 5 | 6-17-AE | 89% PCL 1250 | 11% 25/75 PLC |
| 6 | 50-C | 89% PCL 1250 | 11% PEG 1500 |
| 7 | 53-B | 81% PCL 1250 | 19% Dextran 8800 |
| 8 | 6-22-AA | 50% PCL 1250 | 50% PCL 2000 |
| 9 | 49-C | 82% PCL 1250 | 18% Calcium Stearate |
| 10 | 59-C | 85% PCL 1250 | 15% Calcium Carbonate |
| 11 | 51-G | 89% PCL 1250 | 11% 50/50 PLC |
| 12 | 50-F | 77% PCL 2000 | 23% PEG 1500 |
| 13 | 53-C | 76% PCL 1250 | 24% Dextran 503,000 |

[1]Poly(caprolactone): PCL MW 1250, PCL MW 2000, Aldrich Chemical
[2]Crystallization-Controlling Agents:
poly(ethylene glycols) (PEGS), Aldrich Chemical
calcium carbonate, Sigma Chemical
poly(vinyl alcohol) (PVA), Sigma Chemical
dextrans, Sigma Chemical
glycerol monopalmitate, Pfaltz & Bauer
calcium stearate, Pfaltz & Bauer
poly(lactide-co-caprolactone) (PLC), Birmingham Polym.

Handling. The compositions were tested for handling properties, and ranked according to a subjective rating system that evaluated the compositions based on hardness, stickiness to gloves, cohesiveness, smearability, cohesion to a smooth, epoxy countertop after smearing, and effect of moisture on those properties. After evaluation, a formulation was assigned a number from 1 to 7, corresponding to the following rating system:
1=Close to bone wax (control=Ethicon bone wax)
2=Close, after working by hand
3=Close, but with some decrease in handling properties during wet handling
4=Close, but with poor stability
5=Poor consistency
6=Insufficient viscosity (consistency ranging from taffy to model airplane glue)
7=Hard solid and/or no cohesion
The ratings of the formulations are shown in Table 2, below.

TABLE 2

| No. | I.D. | TIME | |
|---|---|---|---|
| | | Zero ($T_0$) | Day six ($T_6$) |
| 1 | (48-D) | 1 | 1 |
| 2 | (6-22-AG) | 1 | 1 |
| 3 | (6-22-AE) | 1 | 1 |
| 4 | (54-C) | 1 | 1 |
| 5 | (51-E) | 1 | 1 |
| 6 | (50-C) | 2 | 1 |
| 7 | (53-B) | 1 | 2 |
| 8 | (6-22-AA) | 2 | 2 |
| 9 | (48-C) | 2 | 2 |
| 10 | (59-C) | 2 | 2 |
| 11 | (51-G) | 2 | 2 |
| 12 | (50-F) | 1 | 3 |
| 13 | (53-C) | 1 | 3 |

Formulation 2 (77% PCL diol MW 1250, 23% PVA) most closely resembled the control formulation (Ethicon bone wax) in handling properties.

Irradiation tests. The PCL-based formulations were gamma-irradiated to test for changes in properties upon sterilization. In general, the formulations appeared unchanged or slightly improved in consistency (i.e., softer, more uniform and homogeneous) after irradiation. All formulations showed little difference in handling between wet and dry latex gloves before and after irradiation.

The irradiated PCL-based formulations made with the crystallization-controlling agents, PEG 2000, calcium carbonate and poly(vinyl alcohol), exhibited excellent handling properties, both dry and wet, and good room temperature stability.

EXAMPLE 2

In Vivo Testing of Poly(caprolactone)-based Compositions

All the formulations listed in Table 2 hereinabove, except formulations 4, 12 and 13, were examined in vivo using a rabbit tibial defect model. Prior to implantation, the formulations were sterilized by gamma irradiation with a dose of 2.9–3.2 Mrads.

In brief, Adult New Zealand White rabbits of mixed gender, and body weights of 2–4 kg prior to the start of the study were used. The animals were assigned computer-generated random identification (I.D.) numbers. Twelve formulations were tested using two animals per formulation. Two animals received the Ethicon bone wax control formulation (Ethicon, Inc., Somerville, N.J.). Each formulation was tested for its hemostatic potential in a 2–4 mm defect created in the tibia of the rabbit using a dental burr. Each formulation was pressed into the defect and observed for 5 minutes. No bleeding or only minimal seepage of blood observed during the five minute observation was considered good hemostasis. Animals were sacrificed at 7 and 14 days after application so that each formulation could be inspected at necropsy at both time points. For all necropsies, the bone surrounding the defect site was excised.

The formulations were rated according to (i) workability prior to implantation, (ii) implantability, and (iii) demonstrated hemostasis for five minutes. The results of the in vivo tests are shown in Table 3, below. (+=effective hemostasis/poor handling; ++=effective hemostasis/good handling; NT=not tested).

TABLE 3

| | | | In Vivo Results[1] | |
|---|---|---|---|---|
| No./I.D. | Rating | Workability | Rabbit #1 | Rabbit #2 |
| 1 48-D | ++ | slippery but implantable | tough tissue mass near defect | tissue mass covered defect; defect reduced |
| 2 6-22-AG | ++ | excellent consistency | tissue mass near defect; some formulation in tissue around defect site; defect partially closed | nodule of hard tissue at defect; defect not evident |
| 3 6-22-AE | ++ | excellent handling | some formulation in the defect | nodule of hard tissue corresponding to defect site |
| 4 54-C | NT | — | — | — |
| 5 51-E | ++ | hard consistency; extensive manipulation to soften | tissue mass resembling fibrotic capsule near defect site; defect still evident; filled with rust-colored viscous liquid. | large tissue mass covering defect site |
| 6 50-C | ++ | hand working gave good consistency | fragment of formulation (unchanged) near defect site; defect still present with | nodule of hard tissue covering defect site; redness around site |

TABLE 3-continued

| No./I.D. | Rating | Workability | In Vivo Results[1] Rabbit #1 | Rabbit #2 |
|---|---|---|---|---|
| 7 53-B | ++ | good handling | formulation inside loose portion of formulation found; defect reduced in size | tissue mass covered defect site; defect nearly disappeared |
| 8 6-22-AA | + | large chunks; difficult to hand work into homogenous mixture | defect mostly healed | tissue mass distal to defect site; defect mostly healed |
| 9 48-C | ++ | some hand working needed | defect mostly healed; smaller, shallower hole remaining | nodule of hard tissue distal to-defect site; defect mostly healed; small depression remaining |
| 10 59-C | ++ | good consistency and tack | tissue mass present; defect mostly healed | defect not apparent |
| 11 51-G | ++ | good consistency but slightly sticky; slippery when wet | defect partially healed | large nodule of hard tissue distal to defect site; defect partially healed |
| 12 50-F | NT | — | — | — |
| 13 53-C | NT | — | — | — |
| Controls | ++ | | defect apparent; filled with rust-colored viscous fluid | mass of spongy tissue distal to defect site attached to bone by hard tissue; defect healed completely |

[1]Rabbit #1 was sacrificed at 7 days postsurgery; rabbit #2 was sacrificed at 14 days postsurgery.
[2]Rabbit #1 was sacrificed at 9 days postsurgery.
[3]Control was Ethicon bone wax, Ethicon, Inc., Somerville, NJ

EXAMPLE 3

PCL-based Formulations Prepared with Coloring Agent

PCL-based formulation No. 2 (6–22-AG) (77% PCL 1250, 23% PVA) from Table 3 above, was combined with the following dyes: (i) FD&C Blue No. 1 (Warner Jenkinson), used in food, drugs, and cosmetics, except in the eye area; (ii) D&C Green No. 6 (Warner Jenkinson), used in sutures and approved for externally applied drugs and cosmetics; and (iii) D&C Violet No. 2 (Warner Jenkinson). About 0.1 wt-% of the dye was mixed into the formulation during the melting stage.

The PCL-blue dye composition disintegrated in the buffer at about the same time as the undyed specimens. The PCL-green dye formulation and the PCL-violet formulation took slightly longer to disintegrate. The green and violet colored compositions also left some coloration on gloves following handling. The buffer was slightly colored by the blue dye after the blue dyed composition disintegrated, but not by the violet and green dyes which appeared to be bound up in the fragments of those compositions in the buffer.

EXAMPLE 4

In Vitro Release of Bovine Serum Albumin from PCL-based Compositions

A PCL-based composition containing PCL 1250 and 24% poly(vinyl alcohol) was formulated with 1% by weight bovine serum albumin (BSA), a protein used as a model to represent osteoinductive growth factors. The BSA was rolled and kneaded by hand into the solid formulation, which was prepared as described in Example 1, hereinabove.

To assay the release of the BSA from the composition, a small pellet (30–50 mg) of the composition was placed into each of three vials containing phosphate buffered saline (PBS), pH 7.4 (i.e., release solution). The vials were maintained in an environmental shaker at 37° C. to simulate in vivo conditions. The buffer was decanted and replaced at 1, 3, 5, and 7 days. At each point, each of the decanted release solutions were analyzed for the amount of BSA in solution.

The percentage of BSA released from the composition was calculated to generate a release profile of the protein from the composition. In order to detect the BSA in the release solution, reagents that change color in the presence of BSA were combined with the buffer. The intensity of the resulting color was measured spectrophotometrically.

The formulation tested, PCL 1250 MW+poly(vinyl alcohol), fragmented into small flakes after 4–6 hours in the buffer solution at 37° C. The cumulative release of BSA was 21% at day 1, 41% at day 3, 43% at day 5, and 43% at day 7.

EXAMPLE 5

In Vitro Release of Doxycycline Hyclate from PCL-based Compositions

A PCL-based composition containing 30% poly(vinyl alcohol) and several different formulations containing various percentages of PEG 2000 MW were formulated with 10% by weight doxycycline hyclate to test release of the antibiotic from the compositions over time. The doxycycline hyclate was added to each of the molten formulations which were prepared as described hereinabove in Example 1, and after cooling, a 30-50 mg pellet of each formulations was placed in vials containing PBS (pH 7.4), with three samples tested for each formulation.

The release solutions were analyzed for content of doxycycline by UV spectrophotometry. The PCL/PVA formulation fragmented into flakes within about 6 hours in the PBS at 37° C., and 100% of the dorycycline was released from the formulation within 24 hours.

The following formulations were also tested to observe the effect of varying the additive concentration of release of doxycycline:

(i) 90% PCL 1250 with 10% PEG 2000

(ii) 78% PCL 1250 with 22% PEG 2000

(iii) 70% PCL 1250 with 30% PEG 2000

These formulations were tested using PBS, pH 6.85, as the release solution. Formulation (iii) showed the most rapid initial release, with 41% of the drug being released within 24 hours, and 58% of the doxycycline released in 14 days. Formulation (ii) released 30% of its drug load within 24 hours, with 75% release by day 14. Formulation (i) released 40% of its doxycycline after 24 hours, and a total of 83% was released by day 14.

These results indicate that the release profile of the PCL-based formulations may be varied without a significant effect on the handling properties, as all of the above-mentioned formulations possessed handling properties similar to the Ethicon bone wax control.

Compositions containing other hydrophilic drugs may be prepared and used in this same fashion, including, for example, vancomycin, methicillin, and cefazolin. A composition formulated with 79% PCL 1250/21% PEG 2000 and containing 5% vancomycin hydrochloride showed a quick release of the drug over a 20-day period.

EXAMPLE 6

In Vitro Release of Gentamicin Sulfate from PCL-based Compositions

A PCL-based composition containing 15% calcium carbonate and a composition containing 14% 50/50 poly(lactide-co-caprolactone) were formulated with 5% by weight gentamicin sulfate, an antibiotic used for treating osteomyelitis. The formulations were prepared as described in Example 5 hereinabove, and PBS, pH 7.4, was used as the release solution. As gentamicin sulfate has no ultraviolet absorption, the release solutions were derivitized with trinitrobenzene sulfonic acid. This procedure allows the release solutions to be analyzed by UV spectrophotometry.

The calcium carbonate formulation released about 25% of the drug after 24 hours, around 45% in 7 days, and approximately 85% in 28 days. The PCL/PLC formulation released approximately 15% of the gentamicin after 24 hours, about 30% of the drug in 7 days, and about 60% in 28 days.

EXAMPLE 7

In Vitro Release of Ciprofloxacin Hydrochloride from PCL-based Compositions

PCL 1250-based compositions containing 15-40% of a crystallization-controlling agent and 5% ciprofloxacin hydrochloride were prepared according to the procedure described in Example 5 hereinabove. Rough spheres weighing approximately 40 mg of each formulation were placed in vials containing 5 ml PBS, pH 7.4, as the release solution. The vials were maintained at 37° C. in an environmental chamber. At various time points, the release solution was decanted and replaced.

The amount of ciprofloxacin in the release solutions was analyzed by UV spectrophotometry. A composition containing 23% poly(vinyl alcohol), fragmented into small flakes within 6 hours, and released 87.5% of the drug within 7 days, and 95% of the drug within 14 days. A composition containing (i) 40% poly(ethylene glycol) (MW 3350) released 98% of the ciprofloxacin hydrochloride after 28 days; (ii) 30% poly(ethylene glycol) (MW 3350) released 90% of its drug load in 28 days; and (iii) 20% poly(ethylene glycol) (MW 3350) released 62% of the drug in 28 days. A composition containing 15% calcium carbonate released about 42% of the ciprofloxacin hydrochloride after 28 days. All of these formulations exhibited the desired handling characteristics, i.e., moldability, smearability, and uniformity of consistency.

EXAMPLE 8

Larger Scale Preparation of a Poly(caprolactone) Composition with 21% Poly(Ethylene glycol)

A 100 gram batch of a composition containing 79% by weight poly(caprolactone) (molecular weight 1250, Scientific Polymer Products, Inc.) and 21% poly(ethylene glycol) (molecular weight 3350, Dow Chemical Co.) was prepared as follows. A jacketed one-pint, double planetary mixer (Ross 130 LDM, Charles Ross and Son Co.) was heated to 60° C. by circulating water through the mixer jacket using a thermostat-controlled circulating water bath (Model A81, Haake) connected to the mixer jacket by tubing. Poly(caprolactone), 79.00 gms, and poly(ethylene glycol), 21.04 grams, were then added to the mixing bowl, and the mixer was closed and a static vacuum established. When the material was about half melted, the mixer was activated. Once the entire mixture was molten, the mixing bowl temperature was then brought down to 48° C. over about a 120 minute period. Mixing was continued for 1 hour at 48° C. The mixer was then opened and the molten composition was poured into a poly(propylene) cartridge for the filling process. The cartridge was placed in a cartridge holder which was heated with electrical heating tape to keep the mixture molten. The cartridge holder was then connected to the dispenser control unit (Model 1500 XL, EFD).

Portions of 2-3 grams of the composition were then dispersed into heat-sealable pouches. Pouches were made of a polypropylene/polyethylene/aluminum foil material (Bell Fibre Products). The pouches were then laid horizontally in a 37° C. oven. After 24 hours, the pouches were taken out of the oven and allowed to cool to room temperature.

What is claimed is:

1. A biodegradable, pharmaceutical composition, consisting of:

(a) a biodegradable poly(caprolactone) thermoplastic polymer having a weight average molecular weight of about 600–3000; and (b) a biodegradable, crystallization-controlling agent selected from the group consisting of calcium carbonate, hydroxyapatite, calcium phosphate, calcium apatite, calcium sulfate, calcium bicarbonate, calcium chloride, sodium carbonate, sodium bicarbonate, sodium chloride, calcium stearate, calcium palmitate, sodium stearate, dextran, starch, sodium carboxymethyl cellulose, carboxymethyl cellulose, hydroxyethyl cellulose, hydroxypropyl cellulose, cross-linked sodium carboxymethyl cellulose, poly(vinyl alcohol), glycerol palmitate, glycerol stearate, triethyl citrate, ethyl lactate, poly(ethylene glycol), poly(vinyl pyrrolidone), poly(lactide-co-caprolactone), and combinations thereof; wherein the composition contains the crystallization-controlling agent in an amount effective to maintain the poly(caprolactone) as a moldable mass wherein crystalline regions of the poly(caprolactone) polymer are substantially uniformly distributed throughout; and the composition has a spreadable consistency and is capable of adhering to and providing an effective amount of homeostasis in a bone defect.

2. The biodegradable pharmaceutical composition according to claim 1, consisting of about 40–95 wt % poly (caprolactone), and about 5–60 wt % of the crystallization-controlling agent.

3. The biodegradable pharmaceutical composition according to claim 1, wherein the poly(caprolactone) polymer has a weight average molecular weight of about 800–2500.

4. The biodegradable pharmaceutical composition according to claim 1, wherein the crystallization-controlling agent is poly(vinyl alcohol) having a molecular weight of about 5,000–20,000, with a percent hydrolysis of about 80–100%.

5. A biodegradable, pharmaceutical composition, consisting of:
  (a) a biodegradable poly(caprolactone) thermoplastic polymer having a weight average molecular weight of about 600–3000;
  (b) a biodegradable, crystallization-controlling agent selected from the group consisting of calcium carbonate, hydroxyapatite, calcium phosphate, calcium apatite, calcium sulfate, calcium bicarbonate, calcium chloride, sodium carbonate, sodium bicarbonate, sodium chloride, calcium stearate, calcium palmitate, sodium stearate, dextran, starch, sodium carboxymethyl cellulose, carboxymethyl cellulose, hydroxyethyl cellulose, hydroxypropyl cellulose, cross-linked sodium carboxymethyl cellulose, poly(vinyl alcohol), glycerol palmitate, glycerol stearate, triethyl citrate, ethyl lactate, poly(ethylene glycol), poly(vinyl pyrrolidone), poly(lactide-co-caprolactone), and combinations thereof; and
  (c) one or more additives selected from the group consisting of a biologically-active agent, a coloring agent, a release rate modification agent, and a pore forming agent;
wherein the composition contains the crystallization-controlling agent in an amount effective to maintain the poly(caprolactone) as a moldable mass wherein crystalline regions of the poly(caprolactone) polymer are substantially uniformly distributed throughout; and the composition has a spreadable consistency and is capable of adhering to and providing an effective amount of homeostasis in a bone defect.

6. The biodegradable, pharmaceutical composition, of claim 5 wherein the additive is a biologically-active agent, and the biologically-active agent is selected from the group consisting of an anti-inflammatory agent, an antimicrobial agent, an antiparasitic agent, anti-neoplastic agent, an analgesic agent, an anaesthetic agent, a vaccine, a central nervous system agent, a growth factor, a hormone, an antihistamine, an osteoinductive agent, a cardiovascular agent, an anti-ulcer agent, a bronchodilating agent, a vasodilating agent, a birth control agent, a fertilitiy-enhancing agent, and any combination thereof.

7. The biodegradable pharmaceutical composition according to claim 5, wherein the biologically-active agent is an antimicrobial agent selected from the group consisting of an antibacterial agent, an antifungal agent, and an antiviral agent.

8. The biodegradable pharmaceutical composition according to claim 5, wherein the biologically-active agent is a growth factor selected from the group consisting of an osteoinductive growth factor, platelet-derived growth factor, insulin-like growth factor, transforming growth factor $\beta$, fibroblast growth factor, human growth factor, and any combination thereof.

9. The biodegradable pharmaceutical composition according to claim 5, wherein the release rate modification agent is selected from the group consisting of an ester of a monocarboxylic acid, an ester of a dicarboxylic acid, an ester of a tricarboxylic acid, a polyhydroxy alcohol, an ester of a fatty acid, a triester of glycerol, a sterol, an alcohol, and any combination thereof.

10. The biodegradable pharmaceutical composition according to claim 9, wherein the release rate modification agent is selected from the group consisting of 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl) sebecate, propylene glycol, polyethylene glycol, glycerin, sorbitol, triglyceride, epoxidized soybean oil, cholesterol, a $C_6$–$C_{12}$ alkanol, 2-ethoxyethanol, or any combination thereof.

11. The biodegradable pharmaceutical composition according to claim 9, wherein the release rate modification agent is selected from the group consisting of dimethyl citrate, triethyl citrate, ethyl heptanoate, glycerin, hexanediol, and any combination thereof.

12. A biodegradable, pharmaceutical composition, produced by the process of:
  (a) combining a biodegradable poly(caprolactone) thermoplastic polymer with a biodegradable crystallization-controlling agent to form a mixture; the polymer having a weight average molecular weight of about 600–3000; and the crystallization-controlling agent selected from the group consisting of calcium carbonate, hydroxyapatite, calcium phosphate, calcium apatite, calcium sulfate, calcium bicarbonate, calcium chloride, sodium carbonate, sodium bicarbonate, sodium chloride, calcium stearate, calcium palmitate, sodium stearate, dextran, starch, sodium carboxymethyl cellulose, carboxymethyl cellulose, hydroxyethyl cellulose, hydroxypropyl cellulose, cross-linked sodium carboxymethyl cellulose, poly(ethylene glycol), poly(vinyl pyrrolidone), poly(lactide-co-caprolactone), and combinations thereof;
  (b) melting the polymer mixture to a molten mass; and
  (c) cooling the polymer mixture at a temperature of about 30°–50° C. and over a time period of about 1–72 hours to form the biodegradable composition; wherein the composition contains the crystallization-controlling agent in an amount effective to maintain the poly(caprolactone) as a moldable mass wherein crystalline regions of the poly(caprolactone) polymer are substantially uniformly distributed throughout and the composition has a spreadable consistency and is capable of adhering to and providing and effective amount of homeostasis in a bone defect.

13. A method for treating a tissue defect, comprising:

applying an effective amount of a biologically-acceptable, biodegradable composition to the defect, the composition consisting of:

a biodegradable poly(caprolactone) thermoplastic polymer having a weight average molecular weight of about 600–3000, and a biodegradable, crystallization-controlling agent selected from the group consisting of calcium carbonate, hydroxyapatite, calcium phosphate, calcium apatite, calcium sulfate, calcium bicarbonate, calcium chloride, sodium carbonate, sodium bicarbonate, sodium chloride, calcium stearate, calcium palmitate, sodium stearate, dextran, starch, sodium carboxymethyl cellulose, carboxymethyl cellulose, hydroxyethyl cellulose, hydroxypropyl cellulose, cross-linked sodium carboxymethyl cellulose, poly(vinyl alcohol), glycerol palmitate, glycerol stearate, triethyl citrate, ethyl lactate, poly(ethylene glycol), poly(vinyl pyrrolidone), poly(lactide-co-caprolactone), and combinations thereof;

the composition being a moldable mass wherein crystalline regions of the poly(caprolactone) polymer are substantially uniformly distributed throughout; wherein the composition provides an effective amount of hemostasis in the defect, promotes tissue regrowth in the defect, or a combination thereof.

14. The method according to claim 13, further comprising sterilizing the composition prior to applying the composition to the tissue defect.

15. The method according to claim 14, wherein the composition is sterilized using gamma radiation.

16. A method for treating a tissue defect, comprising:

applying an effective amount of a biologically-acceptable, biodegradable composition to the defect, the composition consisting of:

a biodegradable poly(caprolactone) thermoplastic polymer having a weight average molecular weight of about 600–3000;

a biodegradable, crystallization-controlling agent selected from the group consisting of calcium carbonate, hydroxyapatite, calcium phosphate, calcium apatite, calcium sulfate, calcium bicarbonate, calcium chloride, sodium carbonate, sodium bicarbonate, sodium chloride, calcium stearate, calcium palmitate, sodium stearate, dextran, starch, sodium carboxymethyl cellulose, carboxymethyl cellulose, hydroxyethyl cellulose, hydroxypropyl cellulose, cross-linked sodium carboxymethyl cellulose, poly(vinyl alcohol), glycerol palmitate, glycerol stearate, triethyl citrate, ethyl lactate, poly(ethylene glycol), poly(vinyl pyrrolidone), poly(lactide-co-caprolactone), and combinations thereof; and an effective amount of a biologically active agent;

the composition being a moldable mass wherein crystalline regions of the poly(caprolactone) polymer are substantially uniformly distributed throughout; wherein the composition provides an effective amount of hemostasis in the defect, promotes tissue regrowth in the defect, or a combination thereof.

17. A method for treating a tissue defect, comprising:

applying an effective amount of a biologically-acceptable, biodegradable composition to the defect, the composition consisting of:

a biodegradable poly(caprolactone) thermoplastic polymer having a weight average molecular weight of about 600–3000;

a biodegradable, crystallization-controlling agent selected from the group consisting of calcium carbonate, hydroxyapatite, calcium phosphate, calcium apatite, calcium sulfate, calcium bicarbonate, calcium chloride, sodium carbonate, sodium bicarbonate, sodium chloride, calcium stearate, calcium palmitate, sodium stearate, dextran, starch, sodium carboxymethyl cellulose, carboxymethyl cellulose, hydroxyethyl cellulose, hydroxypropyl cellulose, cross-linked sodium carboxymethyl cellulose, poly(vinyl alcohol), glycerol palmitate, glycerol stearate, triethyl citrate, ethyl lactate, poly(ethylene glycol), poly(vinyl pyrrolidone), poly(lactide-co-caprolactone), and combinations thereof;

an effective amount of a biologically active agent; and one or more additives selected from the group consisting of a biologically-active agent, a coloring agent, a release rate modification agent, and a pore forming agent;

the composition being a moldable mass wherein crystalline regions of the poly(caprolactone) polymer are substantially uniformly distributed throughout; wherein the composition provides an effective amount of hemostasis in the defect, promotes tissue regrowth in the defect, or a combination thereof.

* * * * *